United States Patent [19]

Chu et al.

[11] Patent Number: 4,613,604
[45] Date of Patent: Sep. 23, 1986

[54] HYDROXYMETHYL DERIVATIVES OF 5-BENZYLACYCLOURIDINE AND 5-BENZOYLOXYBENZYLACYCLOURIDINE AND THEIR USE AS POTENTIATORS FOR 5-FLUORO-2'-DEOXYURIDINE

[75] Inventors: Shih H. Chu, Barrington; Paul Calabresi, West Barrington; Ming Y. W. Chu, Barrington; Mahmoud H. el Kouni, Providence; Fardos N. M. Naguib, Providence; Sungman Cha, Providence, all of R.I.

[73] Assignee: Brown University Research Foundation, Providence, R.I.

[21] Appl. No.: 761,208

[22] Filed: Jul. 31, 1985

[51] Int. Cl.[4] ................ A61K 31/505; C07D 239/54
[52] U.S. Cl. .................................. 514/274; 544/314
[58] Field of Search ..................... 544/314; 514/274

[56] References Cited

U.S. PATENT DOCUMENTS 4,415,573 11/1983 Ochi et al. ...................... 544/314

FOREIGN PATENT DOCUMENTS 58-39672 3/1983 Japan ............................... 544/314

OTHER PUBLICATIONS

Chu et al., *Cancer Research*, vol. 44, pp. 1852–1856, (1984).

*Primary Examiner*—Donald G. Daus
*Assistant Examiner*—Stephen M. Kapner
*Attorney, Agent, or Firm*—Biebel, French & Nauman

[57] ABSTRACT

A compound of the Formula (I):

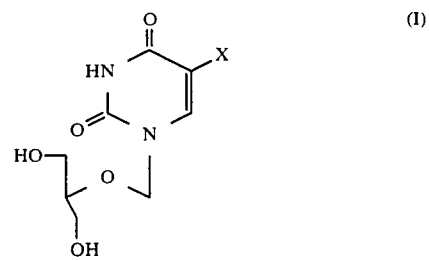

where X is a benzyl group or a benzyloxybenzyl group and pharmaceutical preparations containing the same.

8 Claims, No Drawings

HYDROXYMETHYL DERIVATIVES OF 5-BENZYLACYCLOURIDINE AND 5-BENZOYLOXYBENZYLACYCLOURIDINE AND THEIR USE AS POTENTIATORS FOR 5-FLUORO-2'-DEOXYURIDINE

BACKGROUND OF THE INVENTION

The present invention relates to hydroxymethyl derivatives of 5-benzylacyclouridine and 5-benzoyloxybenzylacyclouridine and to their use in the potentiation of pyrimidine nucleosides such as 5-fluoro-2'-deoxyuridine (FdUrd) in cancer chemotherapy by way of uridine phosphorylase inhibition.

The efficacy of the chemotherapeutic agent FdUrd is limited by its cleavage to the less effective base 5-fluorouracil (Fura). Two enzymes are responsible for the cleavage, thymidine phosphorylase and uridine phosphorylase.

There has been a great deal of interest in developing inhibitors of FdUrd degradation. In contrast to normal tissues, many neoplasms are deficient or have a low activity level of thymidine phosphorylase as compared to uridine phosphorylase. It has been proposed that by coadministering a uridine phosphorylase inhibitor with FdUrd, the activity of FdUrd can be selectively directed against the tumor cells and not against the host tissues. With coadministration of a uridine phosphorylase inhibitor, the host tissues should retain their capacity to cleave FdUrd to FUra by thymidine phosphorylase, but in tumors in which the activity of thymidine phosphorylase is low or absent, with inhibition of uridine phosphorylase, FdUrd retains its efficacy.

A series of acyclouridines have been developed as inhibitors of uridine phosphorylase. See Niedzwicki, et al., "5-Benzylacyclouridine and 5-Benzyloxybenzylacyclouridine, Potent Inhibitors of Uridine Phosphorylase" *Biochem. Pharmacol.*, 31: 1857–1861, 1982 and Niedwicki, et al., "Pyrimidine Acyclonucleoside, Inhibitors of Uridine Phosphorylase," *Biochem. Pharmacol.*, 30:2097–2101, 1981. Among the acyclouridines which have been developed, 5-benzylacyclouridine (BAU) and 5-benzyloxybenzylacyclouridine (BBAU) have been particularly effective. It has been shown that these compounds inhibit the cleavage of FdUrd in certain tumor extracts and enhance the antineoplastic activity of FdUrd on human pancreatic carcinoma (DAN) and human lung carcinoma (LX-1) cell lines in vitro and in vivo. See Chu et al., "Potentiation of 5-Fluoro-2'deoxyuridine Antineoplastic Activity by the Uridine Phosphorylase Inhibitors Benzylacyclouridine and Benzyloxybenzylacyclouridine," *Cancer Res.* 44, 1852–56, May 1984. BAU and BBAU, however, are not very water soluble.

SUMMARY OF THE INVENTION

A principle object of the present invention is to provide novel water soluble uridine phosphorylase inhibitors.

An equally important related object of the present invention is to provide novel water soluble uridine phosphorylase inhibitors which are potentiators of the antitumor activity of pyrimidine nucleosides such as FdUrd and which do not interfere with growth of normal cells of the host.

A specific object of the present invention is to provide novel uridine phosphorylase inhibitors which reduce phosphorolytic degradation of FdUrd to the less active FUra in tumor cells.

These and other objectives are achieved in accordance with the present invention which provides compounds of the Formula (I):

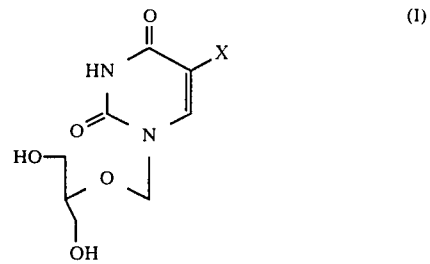

where X is a benzyl group or a benzyloxybenzyl group.
These compounds are:
(1) Hydroxymethylbenzylacyclouridine or 5-Benzyl-1-[(1,3-dihydorxy-2-propoxy)methyl]uracil (hereafter HM-BAU), and
(2) Hydroxymethylbenzyloxybenzylacyclouridine or 5-(m-Benzyloxybenzyl)-1-[1,3-dihydroxy-2-propoxy)methyl]uracil (hereafter HM-BBAU)

One embodiment of the invention relates to a pharmaceutical preparation comprising a compound of the formula (I) in an amount which is effective in inhibiting uridine phosphorylase.

A further embodiment of the present invention is an improvement in chemotherapy with pyrimidine nucleosides such as FdUrd which comprises administering a compound of the Formula (I) in conjunction with the administration of FdUrd or like antineoplastic agents to a host afficted with a tumor.

The compounds of the present invention are particularly advantageous because they are water soluble, they inhibit uridine phosphorylase, and they do not appear to adversely affect normal cell growth. In addition to being useful in potentiating FdUrd, it is anticipated that the compounds of the present invention may also be useful in potentiating other antineoplastic pyrimidine nucleosides which are subject to degradation by uridine phosphorylase.

As potentiators for FdUrd, the compounds of the present invention may be administered in conjunction with FdUrd in established FdUrd therapies. FdUrd has been used in the treatment of colon cancer, pancreatic carcinoma and lung cancer but is limited by the toxicity of its product, FUra, to the host. Those skilled in the art are familiar with the therapies in which FdUrd is used and it is anticipated that HM-BAU and HM-BBAU may be useful in potentiating FdUrd in any of its therapies. The compounds will be particularly effective in potentiating FdUrd in tumors having low or no thymidine phosphorylase activity. Such tumors may be characterized as having a ratio of thymidine phosphorylase to uridine phosphorylase activity less than about 0.4. DAN and LX-1 cells are two examples.

HM-BAU and HM-BBAU are preferably administered prior to FdUrd but may be administered later with reduced effectiveness. The compounds are preferably administered in advance of the antineoplastic agent to inhibit the phosphorylase enzyme and thereby prevent degradation of the anticancer agent.

Because HM-BAU and HM-BBAU are water soluble, they can therefore be administered intravenously in saline solution or saline solution buffered to a pH of 7.2 to 7.5, the physiological range. Conventional buffers such as tris phosphates, bicarbonates or citrates can be used for this purpose.

Effective dosages for the compounds can be determined by routine experimentation--the objective of any administration of the compounds being to inhibit uridine phosphorylase at the site of the tumor. It is anticipated that the compounds will be administered in amounts ranging from about 0.1 to 200 mg/kg body weight per day and more typically 1 to 100 mg/kg/day. The exact amount will vary with the nature of the tumor and the activity of uridine phosphorylase therein. Tumors with lower activity should require lower dosages.

DETAILED DESCRIPTION OF THE INVENTION

Chemical syntheses

HM-BAU and HM-BBAU are synthesized according to Reaction Scheme I.

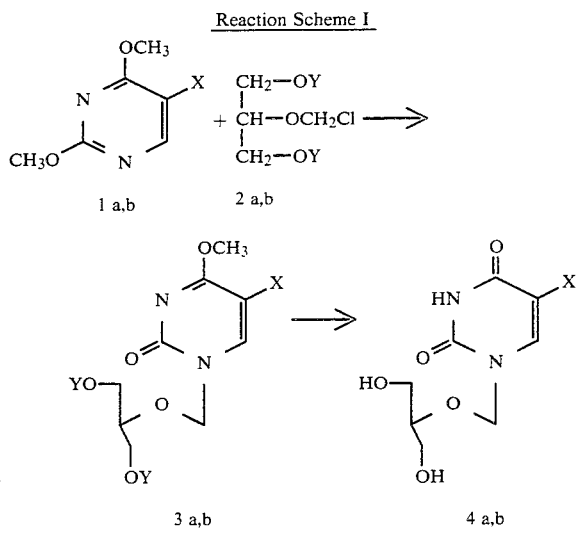

a. $X = Y = C_6H_5CH_2-$
b. $X = m-C_6H_5CH_2OC_6H_4CH_2-$
   $Y = C_6H_5CO-$

Appropriately blocked 2-0-chloromethylated glycerols are condensed with 5-benzyl- or 5-benzyloxybenzyluracil derivatives according to the methods described by C. W. Noell and C. C. Cheng, in *Nucleic Acid Chemistry*, L. B. Townsend and R. S. Tipson, eds., Vol. 1, John Wiley & Sons, New York, 1978; pp 57–66, and M. J. Robins and P. W. Hatfield, *Can. J. Chem.* 60, 547 (1982). The products are then deblocked by catalytic hydrogenation or alkaline hydrolysis. It is necessary to change the blocking group from benzyl (higher yielding) to benzoyl for the BBAU analog, to avoid conversion of BBAU to BAU analogs during deblocking. The possibility of rearrangement of 1,3-glyceryl diesters to 1,2-diesters under the acidic conditions of chloromethylation should be noted. On the basis of NMR spectra, such a rearrangement does not appear to take place, since there is no 2-proton signal at δ 3.5 corresponding to NCOCH$_2$ in the spectrum of 3b. Instead, all of the glyceryl proton signals have been shifted to δ4.47, the location of CH$_2$-OBzoyl in the spectra of BAU and BBAU benzoates. Diethers do not rearrange under these conditions. The synthesis is illustrated in more detail by the following Synthesis Examples:

SYNTHESIS EXAMPLES 1

5-Benzyl-1-[(1,3-bis(benzyloxy)-2-propoxy)methyl]uracil (3a)

1,3-Di-O-benzylglycerol was prepared by treating epichlorohydrin with benzyl alcohol and NaOH. See J. C. Martin, C. A. Dvorak, D. F. Smee, T. R. Matthews and J. P. H. Verheyden, *J. Med. Chem.* 26, 759 (1983). To obtain the chlorinated side chain, hydrogen chloride gas was dried by passage through concentrated sulfuric acid and bubbled into a stirred mixture of paraformaldehyde (0.8 g, 26 mmol) and 1,3-di-0-benzylglycerol (1.5 g, 5.6 mmol) in 20 ml of dry methylene chloride at 0° C. for 3 hrs until all the paraformaldehyde had dissolved. The resulting solution was stored at 0° C. for 16 hrs and then dried over CaCl$_2$. After filtering, solvent and excess HCl were removed in vacuo. The oily residue was dissolved in 20 ml of methylene chloride and added to a mixture of 1a (1 g, 4.3 mmol) finely ground potassium carbonate (1.5 g), and 30 ml of dry methylene chloride. The reaction mixture was stirred overnight under nitrogen at room temperature. After filtering, the solvent was removed under reduced pressure and the residual oil passed through a silica gel column and eluted with methylene chloride-methanol (3:1). Evaporation of solvent then yielded 0.61 g of pure 3a (43%) as a colorless oil. UV(EtOH): λ max 282 nm (5500). NMR(CDCl$_3$): δ3.47–3.60 (m, 6H, CH$_2$OBzl and CH$_2$ at C$_5$ overlap), 3.95 (s, 3H, OCH3), 3.99–4.10 (m, 1H, tert. H) 4.49 (s, 4H, OBzl), 5.35 (s, 2H, CH$_2$ at N$_1$), 7.09–7.37 (m, 16H, ArH and C$_6$-H overlap). Anal. Calc'd for C$_{30}$H$_{32}$N$_2$O$_5$: C, 71.98; N, 6.44; N, 5.60. Found: C,71.80, H,6.50; N, 5.51.

SYNTHESIS EXAMPLE 2

5-Benzyl-1-[(1,3-dihydroxy-2-propoxy)methyl]uracil (4a)

2 g (4.6 mmol) of 3a prepared as above was dissolved in 100 ml of glacial acetic acid and 0.2 ml of concentrated HCl. 5% Palladium on charcoal (1 g) was then added and the reaction mixture hydrogenated under 50 lbs pressure. After the theoretical amount of hydrogen had been absorbed, the solution was filtered and evaporated to dryness. The residue was placed on a silica gel column and eluted with methylene chloride-methanol (12:1) to give 1.1 g of 4a (87%). It was isolated as an oil and dried under vacuum over P$_2$O$_5$ for several days. UV (pH 1): λ max 266 nm (9400); pH 11: λ max 266 nm (6400). NMR(DMSO-d$_6$): δ3.47 (s, 4H, CH$_2$OH), 3.52 (s, 3H, CH$_2$ at C$_5$ and tert. H), 4.66 (t, 2H, OH) 5.20 (s, 2H, CH$_2$ at N$_1$), 7.24 (s, 5H, ArH), 7.65(s, 1H, C$_6$-H), 11.33 (s, 1H, NH).

Anal. Calc'd for C$_{15}$H$_{18}$N$_2$O$_5$.H$_2$O: C,55.55; H,6.22; N,8.64. Found: C,55.27, H,5.82; N, 8.66.

SYNTHESIS EXAMPLE 3

5-(m-Benzyloxybenzyl)-1-[(1,3-bis(benzoyloxy)-2-propoxy)methyl]uracil (3b)

1,3-Di-O-benzoylglycerol was prepared by treating commercially available 1,3-dichloroacetone with sodium benzoate, followed by catalytic reduction of the ketone to alcohol. Dry hydrogen chloride gas was bubbled into a stirred mixture of paraformaldehyde (0.8 g, 26 mmol) and 1,3-di-0-benzoylglycerol (1.5 g) in 20 ml of dry methylene chloride at 0° C. for 3 hrs. After separating water and further drying over CaCl$_2$, the solvent and excess HCl were removed under vacuum. The residue was dissolved in 20 ml of dry methylene chloride, added to a mixture of 1b (1 g, 3.0 mM), potassium carbonate (1.5 g), and 30 ml of dry methylene chloride and stirred overnight at room temperature. After filtering, the solvent was removed under reduced pressure and the residual oil passed through a silica gel column. Elution was with methylene chloride-methanol (30:1) to give 0.7 g of 3b as pure oily product giving a single spot on TLC (34%). UV(EtOH): λ max 275 nm (8000) and 282 nm (7900). NMR(CDCl$_3$): δ 3.38 (s, 2H, CH$_2$ at C$_5$), 3.93 (s, 3H, OCH$_3$), 4.40–4.65 (m, 5H, CH$_2$OBzoyl and tert. H), 5.00 (s, 2H, OBzl), 5.37 (s, 3 2H, CH$_2$ at N$_1$) 6.60–8.07 (m, 20 H, ArH and C$_6$-H).

Anal. Calc'd for C$_{37}$H$_{34}$N$_2$O$_8$: C,70.02; H, 5.40; N, 4.42. Found: C,70.36; H, 5.80; N, 4.36.

SYNTHESIS EXAMPLE 4

5-(m-Benzyloxybenzyl)-1-[(1,3-dihydroxy-2-propoxy) methyl]uracil (4b)

To a solution of 1.0 g of 3b prepared as above in 35 ml of EtOH there was added 33 ml of 2N NaOH and the reaction mixture stirred overnight at room temperature. The solution was neutralized with HCl or alternatively with Dowex 50 (H+), filtered, and the resin washed thoroughly with aqueous alcohol. After evaporation of the combined filtrates, the residue was passed through a silica gel column and the product eluted with methylene chloride-methanol (15:1) to yield 0.45 g of 4b. It was recrystallized with some difficulty from methylene chloride, M.p. 113° C. UV(pH 1): λ max 266 nm (10,600); (pH 11): λ max 267 nm (7700). NMR(CHCl$_3$): δ 3.53–3.69 (m, 7H, CH$_2$ at C$_5$, CH$_2$OH and tert. H overlap), 5.02 (s, 2H, CH$_2$ of OBzl), 5.20 (s, 2H, CH$_2$ at N$_1$), 6.80–7.44 (m, 10H, ArH and C$_6$-H overlap).

Anal. Calc'd. for C$_{22}$H$_{24}$N$_2$O$_6$. 0.75 H$_2$O: C, 62.04; H, 6.03; N, 6.58. Found C, 62.26; H, 5.95; N, 6.84.

Biological Evaluation

Testing of compounds HM-BAU and HM-BBAU as inhibitors of uridine phosphorylase was performed using 105,000×g supernatant of mouse liver and human liver homogenates. Enzyme assays were carried out as described in Niedzwicki et al., *Biochem. Pharm.* 31, 1857 (1982), supra. Apparent K$_i$ values are related to K$_i$ by the following equation:

$$\text{apparent } K_i = \frac{K_{is}(1 + [S]/K_m)}{1 + ([S]/K_m)(K_{is}/K_{ii})}$$

where K$_{is\ and\ Kii}$ are the inhibition constants that would have been estimated from the replots of slope and intercept, respectively, of a Lineweaver-Burk plot vs [I]. If a compound is a competitive inhibitor with respect to the substrate uridine. K$_{ii}$=∞ and K$_{is}$=K$_i$. Therefore:

$$\text{apparent } K_i = K_i(1 + [S]/K_m)$$

Thus, the true K$_i$ values would be lower than the apparent K$_i$ values by a factor of (1+S/K$_m$). It must be noted, however, that these compounds were not characterized with regard to the type of inhibition (i.e. competitive, non-competitive or uncompetitive), nor were they tested as substrates for uridine phosphorylase.

Apparent K$_i$ values of 1.60 and 0.32 μM were estimated for HM-BAU and HM-BBAU, respectively, for enzyme from mouse liver. When tested against uridine phosphorylase from human liver, the two compounds HM-BAU and HM-BBAU were confirmed as excellent inhibitors of this enzyme and superior to BAU and BBAU; Apparent K$_i$ values being 2.5 and 0.65 μM, respectively.

Determination of the activities of HM-BAU and HM-BBAU as potentiators of FdUrd anti-neoplastic activity was carried out using a human pancreatic carcinoma (DAN) in culture. Details of the procedure are described in Chu et al., supra. Table 1 summarizes the effect of HM-BAU and HM-BBAU upon the inhibitory effect of FdUrd on the growth of pancreatic DAN cells in culture.

TABLE 1

| | % Growth Inhibition of DAN cells in culture | | |
|---|---|---|---|
| | | Potentiator | |
| FdUrd μM | None | HM-BAU 50 μM | HM-BBAU 50 μM |
| 0.1 | 20.2 ± 1.1$^a$ | 63.4 ± 1.1$^a$ | 73.6 ± 0.3$^a$ |
| 0.3 | 33.8 ± 1.3 | 67.8 ± 1.7 | 83.2 ± 1.3 |
| 1.0 | 66 ± 1.4 | 100 | 100 |

$^a$Significantly different at P < 0.001 from control value and p < 0.01 from one another.

FdUrd alone at 0.1 and 0.3 μM inhibited the cell growth by 20% and 34% respectively. However, when 50 μM HM-BAU was added 5 minutes prior to the addition of FdUrd, the growth inhibition by 0.1 and 0.3 μM FdUrd increased significantly (P <0.001) to 63 and 68% respectively. HN-BBAU (50 μM) was even more effective, increasing growth inhibition to 74 and 83%. At 1.0 μM FdUrd there was a 66% inhibition by FdUrd alone, which was enhanced to 100% or greater cell-kill (in addition to inhibition of growth) by pre-treatment with either HM-BAU or HM-BBAU.

The present results demonstrate that the in vitro anti-neoplastic activity of FdUrd can be significantly potentiated by the uridine phosphorylase inhibitors HM-BAU and HM-BBAU. HM-BAU and HM-BBAU alone at 50 μM concentration do not affect the growth of DAN in culture; instead the cytotoxic effects of Fdurd (at 0.1 μM) are enhanced from 20% to 63 and 74% respectively; and of FdUrd (0.3 μM) from 34% to 60 and 83%.

Having described the invention in detail and by reference to preferred embodiments thereof, it will be apparent that modifications and variations are possible without departing from the scope of the invention defined in the appended claims.

What is claimed is:

1. A compound of the Formula (I):

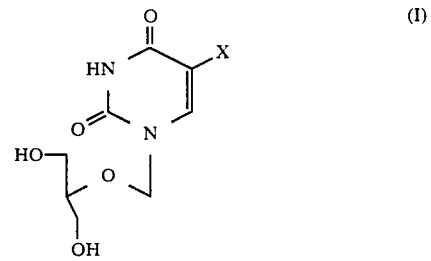

where X is a benzyl group or a benzyloxybenzyl group.

2. The compound of claim 1 wherein X is a benzyl group.

3. The compound of claim 1 wherein X is a benzyloxybenzyl group.

4. A pharmaceutical preparation comprising a uridine phosphorylase inhibiting effective amount of the compound of Formula (I):

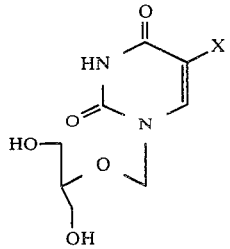

(I)

where X is a benzyl group or a benzyloxybenzyl group and a pharmaceutically acceptable carrier.

5. The pharmaceutical preparation of claim 4 where said carrier is saline solution.

6. The pharmaceutical preparation of claim 5 where X is a benzyl group.

7. The pharmaceutical preparation of claim 5 where X is a benzyloxybenzyl group.

8. The pharmaceutical preparation of claim 5 wherein said preparation is buffered to the physiological range.

* * * * *